United States Patent [19]

Chupp et al.

[11] 4,440,964
[45] Apr. 3, 1984

[54] SUBSTITUTED 2-ALKYLSULFONYLALKYL NITROBENZENES AND PROCESS FOR THEIR PREPARATION

[75] Inventors: John P. Chupp, Kirkwood; Gerhard H. Alt; Terry M. Balthazor, both of University City, all of Mo.

[73] Assignee: Monsanto Company, St. Louis, Mo.

[21] Appl. No.: 358,774

[22] Filed: Mar. 17, 1982

[51] Int. Cl.$^3$ ............................................. C07C 131/00
[52] U.S. Cl. ................................. 568/30; 260/465 R; 560/16
[58] Field of Search ....................... 568/27, 30, 33, 34, 568/35

[56] References Cited

U.S. PATENT DOCUMENTS

| 3,471,474 | 10/1969 | Ekstrom et al. | 260/239.1 |
| 3,689,567 | 9/1972 | Shen et al. | 568/28 X |
| 4,097,526 | 6/1978 | Chan | 568/28 X |
| 4,248,795 | 2/1981 | Chan | 568/28 X |

FOREIGN PATENT DOCUMENTS 44209 1/1982 European Pat. Off. .
1178279 1/1970 United Kingdom .

OTHER PUBLICATIONS

Golinski et al., Tetrahedron Letters, No. 37, pp. 3495 to 3498, (1978).
Harlow et al., Chem. Abs., vol. 81, 1974, p. 503, Abs. No. 127596u.
Makosza et al., Chem. Abs., vol. 95, 1981, p. 636, Abs. No. 95:132497p.

Primary Examiner—Leland A. Sebastian
Attorney, Agent, or Firm—Richard H. Shear; William I. Andress; Robert B. Martin

[57] ABSTRACT

The disclosure herein relates to substituted 2-alkylsulfonylalkyl nitrobenzenes and a process for the preparation thereof. The compounds herein are useful as intermediates in the preparation of certain substituted anilines used as reactants in the preparation of 2-haloacetanilide herbicides.

10 Claims, No Drawings

SUBSTITUTED 2-ALKYLSULFONYLALKYL NITROBENZENES AND PROCESS FOR THEIR PREPARATION

BACKGROUND OF THE INVENTION

1. Field of the Invention

The invention herein pertains to the field of chemical intermediates as the title compounds, useful for the preparation of substituted anilines which are precursor materials for known 2-haloacetanilide herbicides.

2. Description of the Prior Art

Prior art methods for the preparation of substituted nitrobenzenes include the oxidation with peracids of the corresponding optionally-substituted anilines (W. D. Emmons, J.A.C.S 76 3470 (1954) et seq.). Alkylation of sulfones is known, including activated sulfones, such as beta-keto sulfones (Samuelsson et al Acta Chem. Scand. 25, 1555 (1971) and halomethylsulfones (Makosza et al Journal of Org. Chem. 40, 266 (1975). Hydrogenation of nitro-aromatics is well known (see Catalytic Hydrogenation by R. L. Augustine, pp 91, 92, Marcel Dekker, Inc., N.Y. (1965), with a wide variety of anilines therefrom.

U.S. Pat. No. 4,006,183 describes substituted ortho-methylsulfinyl methylanilines by reacting the corresponding substituted ortho-methylthiomethyl anilines with an oxidizing agent, such as $H_2O_2$ in the presence of a peracid. In the process of the '183 patent, the oxidation does not convert the amino group to a nitro group or the methylthiomethyl group to a methylsulfonylalkyl group as in the present process. Similar o-methylsulfinylmethyl anilines as in the '183 patent are disclosed in U.S. Pat. No. 3,996,371 and these anilines are similarly prepared by oxidation of the corresponding o-methylthiomethyl aniline, again without formation of nitro groups or o-methylsulfonyl methyl groups as herein. The '371 patent refers to an article by Claus et al, Monatch Chem. 102, 1571-1582 (1971) for the procedures for preparing said o-methylsulfinyl methylanilines.

Substituted anilines prepared from the corresponding o-alkylsulfonylalkyl nitrobenzenes of this invention are useful as intermediates for the production of the corresponding N-substituted-2-haloacetanilide herbicides. Illustrative prior art disclosing the preparation of said 2-haloacetanilides from said anilines includes U.S. Pat. Nos. 4,258,196 and 3,966,811, British Specification No. 2,013,188, Belgian Patent No. 887,997 and Swiss Patent No. 579,348.

SUMMARY OF THE INVENTION

The present invention relates to a new class of substituted nitrobenzenes useful in the production of substituted anilines used in the preparation of herbicidal N-substituted 2-haloacetanilides.

In more particular, the substituted nitrobenzenes of this invention are characterized by the formula

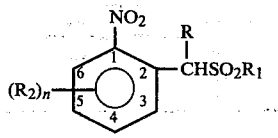

I wherein R is hydrogen, $C_{1-6}$ alkyl or alkanoyl, formyl or alkenyl or alkynyl having up to 4 carbon atoms;

$R_1$ is $C_{1-6}$ alkyl, phenyl or phenyl substituted with $C_{1-6}$ alkyl or alkoxy or halogen;

$R_2$ is independently the same as R or $R_1$, $NO_2$, CN, $CF_3$ or $C_{1-6}$ alkoxy or alkoxycarbonyl and n is 0–4.

Preferred compounds according to Formula I include those wherein R is hydrogen or $C_{1-6}$ alkyl and $R_1$ is also a $C_{1-6}$ alkyl radical. More preferred R and $R_1$ groups are primary alkyl groups, especially the methyl and ethyl radicals; less preferred are secondary and tertiary alkyl groups which may tend to reduce facility of the alkylation reaction by which the product is formed. Preferred $R_2$ members are hydrogen and $CF_3$ in the 6 position. Preferred species according to this invention are 2-(methylsulfonylmethyl)-6-trifluoromethyl nitrobenzene and 2-(1-methylsulfonylethyl)-6-trifluoromethyl nitrobenzene.

Another aspect of this invention is the provision of novel processes for preparing the nitrobenzenes of Formula I. Formula I compounds wherein R is alkyl or alkanoyl having up to 6 carbon atoms, formyl or alkenyl or alkynyl having up to 4 carbon atoms, are prepared by reacting a compound of Formula II.

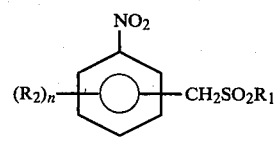

II wherein R, $R_2$ and n are as defined above, with a compound of the formula

RZ  III wherein R is as defined above except hydrogen; and Z is halogen, sulfate or sulfonate radical, such as tosyl, or RZ is a Michael 1,4-addition agent; such agent is a compound of the formula $CH_2=CH-A=B$, wherein A is an atom in Mendeleev's periodic table more electropositive than B; examples of such agents include acrolein, acrylonitrile, methylacrylate, nitroethene, nitropropene, etc.

The reaction between the compounds of Formulae II and III is conducted under basic conditions in an inert solvent, preferably in the presence of a phase transfer catalyst, at temperatures within the range of $-78°$ C. to $150°$ C., and more preferably at temperatures from about $-10°$ C. to $80°$ C. Preferred reactants of Formula III ("alkylating agents") include alkyl sulfates, alkyl halides and alkyl tosylates, wherein the alkyl radicals have up to 6 carbon atoms. Exemplary alkylating agents include alkyl halides, such as the methyl, ethyl, propyl, butyl, pentyl and hexyl bromides, chlorides and iodides; alkyl sulfates and sulfonates, such as the methyl, ethyl, propyl, butyl, pentyl and hexyl sulfates and sulfonates.

Other alkylating agents include alkenyl and alkynyl halides such as the allyl and butenyl bromides, chlorides and iodides, propargyl and methyl-substituted propargyl bromides, chlorides and iodides. Still other alkylating agents are aldehydes such as formaldehyde, acetaldehyde, propanal, butanal, pentanal and hexanal.

Suitable phase transfer catalysts are those containing organic-soluble cations such as those enumerated in U.S. Pat. No. 3,992,432, including ammonium, phosphonium and sulfonium salts. Exemplary phase transfer catalysts include quaternary ammonium salts, such as aryl or aralkyl trialkyl ammonium halides, typified by benzyl triethyl ammonium bromide, chloride or iodide. Other phase transfer catalysts include the acyclic and cyclic poly ethers which complex with the cation of the base and then pair with the anion of the nitrobenzene substrate as counter ion for transport to the organic phase for alkylation. Examples of such polyethers are bis(alkoxyalkyl) ethers, such as bis(methoxyethyl) ether, bis(ethoxyethyl) ether, bis(methoxypropyl) ether, etc. Examples of cyclic ethers are the "18-crown-6" cyclic ether in combination with an alkali hydroxide base, such as potassium hydroxide.

Suitable bases include organometallics, such as lithium alkyls, alkali metal hydrides, hydroxides, and alkoxides and alkaline earth oxides and hydroxides, e.g., sodium or potassium hydride, hydroxide, methoxide or ethoxide, calcium oxide and hydroxide, etc.

Solvents which are useful herein should be inert under reaction conditions; examples of such solvents are various esters of alkanoic acids and alkanols such as the (m)ethyl, propyl, butyl acetates, etc., methyl, ethyl, propyl, butyl, aryl and hexyl alcohols, etc.; dialkyl ethers, e.g., dimethyl-, diethyl- and dipropyl ether; various hydrocarbons and halogenated hydrocarbons such as benzene, toluene, the xylenes, dichloroethylene, dichloroethane; and other well-known solvents such as dimethylsulfoxide, dimethylformamide, tetrahydrofuran, etc. When aqueous bases are used, the solvent should be appreciably water-insoluble.

Another aspect of the invention involves a preliminary process step to prepare compounds according to Formula I above wherein R is hydrogen. This process step comprises reacting a compound of the formula

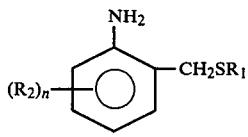

IV wherein $R_1$, $R_2$ and n are as defined above, with a peracid under conditions which convert the amino to a nitro group and the alkylthiomethyl group to an alkylsulfonyl-methyl group.

The reaction is preferably conducted at temperatures below about 75° C. The preferred peracid is peracetic acid, but other peracids, e.g., pertrifluoroacetic acid or perbenzoic acid may be used. The peracid may be used alone or in combination with other oxidizing agents such as hydrogen peroxide.

DETAILED DESCRIPTION OF THE INVENTION

The invention herein involves the preliminary step of oxidizing compounds according to Formula IV with a peracid to form compounds according to Formula II, which in turn are reacted with an alkylating agent of Formula III to form the product of Formula I.

In prior art processes involving oxidation of compounds similar to those in Formula IV, the oxidation did not effect oxidation of the amino group to the corresponding nitro group and the alkylthiomethyl group was converted to an alkylsulfinylmethyl group, rather than an alkylsulfonylmethyl group as herein. Accordingly, the preliminary oxidation process herein results in novel compounds having an important utility as a precursor reactant in a process leading to substituted anilines required to produce the corresponding N-substituted 2-haloacetanilides which are important herbicides.

EXAMPLE 1

This example describes the preparation of 2-methylsulfonylmethyl-6-trifluoromethyl nitrobenzene. In paragraph (1) is described a process for preparing 2-methylthiomethyl-6-trifluoromethyl aniline, the starting material used to prepare said nitrobenzene and paragraph (2) describes the oxidation of said aniline to said nitrobenzene. The reaction in paragraph (1) involves a sulfilimine rearrangement reaction and is analogous to similar processes known in the art, see e.g., Monatsh Chem. 101, 396 (1970), P. Claus et al.

(1) In a 2-liter flask with stirrer is placed 147 g o-(trifluoromethyl)aniline, 250 g $P_2O_5$ and 1 liter $CH_2Cl_2$. With vigorous stirring simultaneously and separately, 250 mL dimethyl sulfoxide and 200 g triethyl amine were added dropwise at such a rate as to create gentle reflux; addition time ca 1 hour with reflux at 41°–42° C., and final temp 52° C. Fifteen minutes after completion of addition, temperature was still 51° C., but external heat was applied for 3 hours, then let stand overnight. Monitoring the reaction by glc was only partially successful; there was decrease in starting aniline and an increase in product peak (sulfilimine decomposing on column to ortho-rearranged product). After reaction, 10% caustic was added to fill flask, then layers separated. Caustic layer washed once with more $CH_2Cl_2$, then combined organic layers washed with water (salt added). The organic layer was stripped of solvent, heated (in kugelrohr) to ca 140°–150° C. for ca ½ hour. The material was distilled through 6" vigreux to give 100 g distillate, bp 60°–100° C. (0.3 mm). A more viscous oil 9.2 g was collected bp 140° C. (0.25–0.45 mm). A second distillation gave 80 g of 2-methylthiomethyl-6-trifluoromethyl aniline, bp 68°–78° C. (0.1 mm Hg).

(2) The oxidation of the substituted aniline prepared in paragraph (1) is exothermic and on a large scale should be conducted at lower reaction temperatures. The order of addition of reactants is important and must be followed as described below.

To a rapidly stirred solution of 40% peracetic acid (200 mL) is added 2-methylthiomethyl-6-trifluoromethyl aniline (48.0 g, 0.217 mmol). The reaction temperature is maintained at <60° C. with an ice/water bath. After complete addition the solution is deep green in color. The solution is heated at ca 90° C. until the color of the solution is orange-brown, ca 2 hr. (the green color is the compound 2-methylsulfonylmethyl-6-trifluoromethyl nitrobenzene). The cooled solution is poured onto 700 mL of ice/water. A yellow solid is formed. This is collected, washed with water and dried. The solid is washed with ether and dried to give 39.75 g (68.6%) of 2-methylsulfonylmethyl-6-trifluoromethyl nitrobenzene; mp 110°–113° C.

| Anal. for $C_9H_8F_3NO_4S$ (wt %) | | |
|---|---|---|
| Element | Theory | Found |
| C | 38.16 | 38.27 |
| H | 2.85 | 2.74 |
| N | 4.95 | 4.86 |

The above oxidation serves the dual function of activating the carbon atom of the methylthiomethyl moiety that is bonded to the ring (i.e., the α-carbon of the benzylic structure) for subsequent anion formation in the alkylation process (described below) and serves as a protecting mechanism for the amino group, i.e., prevent N-alkylation in favor of α-carbon alkylation.

EXAMPLE 2

This example describes the alkylation (methylation) of the product of Example 1(2) under phase transfer conditions to produce the corresponding product methylated on the benzylic α-carbon.

A mixture of $CH_2Cl_2$ (25 mL), $(CH_3)_2SO_4$ (1.92 mL, 20.3 mmol), 2-methylsulfonylmethyl-6-trifluoromethyl nitrobenzene (5.0 g, 17.65 mmol), 50% NaOH (25 mL) and triethylbenzylammonium chloride (20 mg) was rapidly stirred for 35 min. Water (200 mL) and $CH_2Cl_2$ (200 mL) were added and the organic layer separated. The organic layer was washed with 5% HCl, dried ($MgSO_4$) and the solvent removed to give a tacky solid. Excess $(CH_3)_2SO_4$ was removed under high vacuum. Crystallization from EtOAc/hexane gave 2.4 g (8.1 mmol, 45.7%) of a white solid, mp 128°–130° C.

| Anal. Cal'd for $C_{10}H_{10}F_3NO_4S$ (wt %) | | |
|---|---|---|
| Element | Theory | Found |
| C | 40.40 | 40.09 |
| H | 3.40 | 3.28 |
| N | 4.71 | 4.64 |

The product was identified as 2-(1-methylsulfonylethyl)-6-trifluoromethyl nitrobenzene.

EXAMPLE 3

This example describes an alternative methylation system using sodium hydride as the base and methyl iodide as the alkylating agent.

In a dried flask was placed NaH/oil (1.398 g, 17.48 mmol). This was washed with ether (3×60 mL). Diglyme (15 mL) and methyl iodide (1.19 mL, 19.07 mmol) were added and the mixture cooled to 0° C. A diglyme (10 mL) solution of 2-methylsulfonylmethyl-6-trifluoromethyl nitrobenzene (4.5 g, 15.89 mmol) was added dropwise; there was an immediate red color. After complete addition, the solution was stirred five minutes and water (0.5 mL) was added cautiously. Methylene chloride (80 mL) was added and the solution dried ($MgSO_4$). The solvent was removed and the residue subjected to high vacuum to remove diglyme. The solid residue was washed with ether to give 3.2 g, (10.76 mmol), 67.7%) of a white solid, identified as the same product as in Example 2.

The use of a phase transfer catalyst in the alkylation reaction herein represents the preferred manner of carrying out the alkylation. In embodiments using such catalysts, a multiphase system is established wherein a base is present. The cation of the phase transfer catalyst forms an ion pair with the anion of the substituted-alkylsulfonyl-methyl nitrobenzene (negative charge on the benzylic α-carbon) and the ion pair is transported into the organic phase wherein most of the alkylating agent (i.e., compound of Formula III above) resides and so reacts.

The basic material used in the alkylation reaction should be sufficiently strong to react with the starting nitrobenzene, optionally dissolved in an organic solvent, mainly at the interface, to produce incremental concentrations of the benzylic anion for pairing with the cation of the phase transfer catalyst and transport to the organic phase as described above. It will be appreciated that the weaker the acidity of the benzylic anion of the compound of Formula II, the stronger must be the base. When aqueous caustic is used, it is preferred that the solution be concentrated, i.e., 20–50% by weight.

The substituted 2-alkylsulfonylalkyl nitrobenzenes are useful in the preparation of substituted anilines required to make known herbicidal 2-haloacetanilide products of the type exemplified above. Those anilines are prepared by sequentially reducing the nitro group in the substrate nitrobenzene to an amino group. This reduction may be accomplished in situ or by first isolating the 2-alkylsulfonylalkyl nitrobenzene, as in Examples 4 and 5. The 2-alkylsulfonylalkyl group is then transformed to an alkyl group by reductive desulfurization. Those processes are described in Examples 8 and 9 below.

EXAMPLE 4

A mixture of 50% NaOH (50 mL), $CH_2Cl_2$ (50 mL), triethylbenzylammonium chloride (30 mg), $Me_2SO_4$ (2.50 mL, 26.41 mmol) and 2-methylsulfonylmethyl-6-trifluoromethyl nitrobenzene 3 (6.8 g, 24.01 mmol) was stirred rapidly for 30 min. The mixture was poured onto ice/water (400 mL) and the organic layer separated. The solvent was removed and excess $Me_2SO_4$ removed at 60° C. and 0.7 mm, to give a yellow solid which was identified as the same product as in Example 2, i.e., 2-(1-methylsulfonylethyl)-6-trifluoromethyl nitrobenzene. The solid was transferred to a Parr bomb with EtOAc/EtOH (2:1, 100 mL, not all soluble). Five drops of acetic acid and Pd/carbon was added. The mixture was hydrogenated at 60° C. and 60 psi $H_2$ for 15 hrs. The mixture was filtered and the solvent removed to give a brown solid. Washing with ether gave 4.03 g (15.07 mmol, 62.8%) of 2-(1-methylsulfonylethyl)-6-trifluoromethyl aniline as a white solid, mp 153°–5° C.

| Anal. calc'd for $C_{10}H_{12}F_3NO_2S$ (wt %) | | |
|---|---|---|
| Element | Theory | Found |
| C | 44.93 | 44.86 |
| H | 4.53 | 4.47 |
| N | 5.24 | 5.14 |

EXAMPLE 5

Following substantially the same procedure as described in Examples 2 and 4, but using a different alkylating agent, i.e., diethyl sulfate, there is first produced the product 2-(1-methylsulfonylpropyl)-6-trifluoromethyl nitrobenzene.

| Anal. calc'd for $C_{11}H_{12}F_3NO_4S$ (wt. %) | | |
|---|---|---|
| Element | Theory | Found |
| C | 42.44 | 42.46 |
| H | 3.89 | 3.89 |
| N | 4.50 | 4.49 |

The above product is, in turn, reduced to the corresponding aniline, per Example 4, to give white solid m.p. 111°–115° C.

| Anal. Calc'd for $C_{11}H_{14}F_3NO_2S$ (wt. %): | | |
|---|---|---|
| Element | Theory | Found |
| C | 46.97 | 46.92 |

| Anal. Calc'd for $C_{11}H_{14}F_3NO_2S$ (wt. %): | | |
|---|---|---|
| Element | Theory | Found |
| H | 5.02 | 5.02 |
| N | 4.98 | 4.96 |

The product was identified as 2-(1-methylsulfonylpropyl)-6-trifluoromethyl aniline.

Examples 6 and 7 below describe a process for preparing typical 2-alkylsulfonylalkyl-6-trifluoromethyl anilines useful as substrates for transformation to the corresponding aniline by electrolytic reductive desulfurization.

EXAMPLE 6

To a cold stirred $CH_2Cl_2$ (400 ml) solution of 2-methylthiomethyl-6-trifluoromethyl aniline (30 g, 135.6 mmol) was slowly added 3-chloroperbenzoic acid (46.8 g, 271.17 mmol). After two hours, the solution was extracted with 10% NaOH (2×100 mL), dried ($MgSO_4$) and the solvent removed to give a white solid. This was washed with ether to give 28.97 g (114.4 mmol, 84.36%) of 2-methylsulfonylmethyl-6-trifluoromethyl aniline as a white solid, mp 96°–98° C.

| Anal. Calc'd for $C_9H_{10}F_3NO_2S$ (wt. %) | | |
|---|---|---|
| Element | Theory | Found |
| C | 42.68 | 43.09 |
| H | 3.99 | 3.99 |
| N | 5.53 | 5.51 |

EXAMPLE 7

Following the procedure in Example 6, there is also prepared 2-methylsulfonylmethyl-4-chloro-6-trifluoromethyl aniline, a white solid, m.p. 170°–174° C.

| Anal. Calc'd for $C_9H_9ClF_3NO_2S$ (wt. %) | | |
|---|---|---|
| Element | Theory | Found |
| C | 37.57 | 37.57 |
| H | 3.16 | 3.10 |
| N | 4.87 | 4.90 |

The 2-alkylsulfonylalkyl-substituted-nitrobenzenes of the invention may also be reduced to the corresponding 2-alkyl-substituted anilines by electrolytic means. In fact, certain anilines, e.g., 2-ethyl-6-trifluoromethyl aniline is best prepared by electrolysis of the product of Example 2 above, i.e., 2-(1-methylsulfonylethyl)-6-trifluoromethyl aniline. Also, electrolysis of 2-methylsulfonylmethyl-6-trifluoromethyl aniline (the product of Example 6 above) is one of the better ways of producing 2-methyl-6-trifluoromethyl aniline, another important aniline raw material for certain N-substituted 2-haloacetanilide herbicides. Examples 8 and 9 below exemplify electrolysis processes for reducing compounds according to this invention to substituted anilines.

EXAMPLE 8

An electrolysis was conducted to convert 2'-(1-methylsulfonylethyl)-6'-trifluoromethylaniline to 2-ethyl-6-trifluoromethylaniline. The electrolysis was conducted in a cell adapted for incremental addition of the reactant during the electrolysis, with extraction of product during the electrolysis. The initial charge was 125 grams of the reactant compound in 3 liters of an electrolyte which was a 50/50 weight mixture of acetonitrile and an aqueous solution of 1,6-bis(dibutylethylammonium) hexane hydroxide. Electrolysis was conducted at currents of 10–20 amperes in a series of electrolytic procedures, with addition of about 50–100 grams additional reactant each hour, as needed to maintain a reactant concentration of about 125 grams for 3 liters. The aqueous solution used as part of the catholyte contained from about 600 to 1,000 milliequivalents of the specified quaternary ammonium hydroxide, with the actual strength varying for different procedures, but apparently without affecting results significantly. In the electrolyses, the addition of reactant generally occurred over about 5 hours, which was followed by an additional 4 hours or so reaction period with some variation depending upon the current utilized and process parameters monitored. The total reactant in each electrolysis run was 350 to 400 grams. Toward the end of an electrolysis run it was evident that there was a build-up of methanesulfinic acid to gradually neutralize the catholyte, and there was gassing at the cathode. The sulfone reactant had solubility in the catholyte close to 5% by weight, and approximately a 4% concentration was used during an electrolysis run.

Toward the end of a typical electrolysis the sulfone reactant concentration had declined to about 0.4%, while the product had been removed to an extent that its concentration was about 0.2%. The product was removed by counter-current extraction of a catholyte stream with n-hexane. There was some build-up of difluoro compounds, as the hexane was somewhat selective for the desired product over the difluoro compounds. In a series of electrolysis runs generally as described in this example, a total of 5,025 grams was processed, and the extracted product combined for distillation. The distillation yielded 2,250 grams of 2-ethyl-6-trifluoromethylaniline of 98% purity. The 2,250 grams calculates as a 63% chemical yield. The distillation left a large amount of still bottoms, which may have contained starting sulfone compound and difluoromethyl compounds. The electrolysis cell used in these runs was fabricated from parts including a cylindrical glass container about 25.4 cm in diameter having a 1 cm deep mercury pool on the bottom as a cathode (450 cm²), with an insulated copper electrical connection. A 17.8 cm glass tube, with bottom fitted with a Nafion ®427 cation exchange membrane served as the anode compartment. The tube was equipped with a flange at the bottom, and nylon bolts through the flange supported the anode chamber about 1.0 to 1.5 cm above the cathode surface. An expanded metal DSA (dimensionally stable anode, Electrode Corporation TIR-200), 16.5 cm in diameter was mounted horizontally above the membrane. A catholyte circulation system terminated with a sprinkler head dispenser in the middle of the mercury pool, providing radial mass transfer across the cathode surface. A portion of the catholyte was circulated to the top of a packed column for hexane extraction of product, with return of catholyte to the cell. The hexane was continuously distilled from a reboiler pot and entered the column under gravity feed at the bottom, overflowing from the top to return to the reboiler pot. A current of 20 amperes (45 milliamperes/cm²) required a cell voltage of about 5–8 volts.

The 2-(1-methylsulfonylethyl)-6-trifluoromethyl aniline for use as reactant in Example 8 can be obtained by treating 2-methylthiomethyl-6-trifluoromethylaniline with 40% peracetic acid, to oxidize the sulfide group to a sulfonyl group, and also oxidizing the amino group to a nitro group, reacting the resulting compound with dimethylsulfate, using benzyl triethylammonium halide as a phase transfer catalyst, and then hydrogenating to reduce the nitro group and obtain the desired 2-(1-methylsulfonylethyl)-6-trifluoromethylaniline, as described in Examples 1(2), 2 and 4 above. If desired, the nitro group can be reduced at the cathode as a prelude to the electrolysis of the resulting aniline.

EXAMPLE 9

Electrolysis of 2-methylsulfonylmethyl-6-trifluoromethylaniline, 20 grams, in 200 ml of 1 molar tetrabutylammonium hydroxide was conducted in an electrolysis cell with a cadmium cathode. Conversion was very slow, so after 0.66 hours, a lead cathode was substituted. After an additional 2.66 hours, the total conversion to 2-methyl-6-trifluoromethyl aniline was about 23%.

It will be appreciated by those skilled in the art that the invention herein may be modified in non-inventive variations having reference to optimizing process conditions of times, pressures, temperatures, solvents, catalysts, etc., not specifically mentioned herein, but adapted to particular species of starting materials, intermediate and final products without departing from the purview of the invention.

We claim:

1. Compounds having the formula

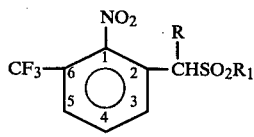

wherein
R is hydrogen or methyl;
$R_1$ is $C_{1-6}$ alkyl, phenyl or phenyl substituted with $C_{1-6}$ alkyl or alkoxy or halogen.

2. Compounds according to claim 1 wherein $R_1$ is a $C_{1-6}$ alkyl radical.

3. Compounds according to claim 1 wherein $R_1$ is a methyl radical.

4. Process for preparing compounds having the formula

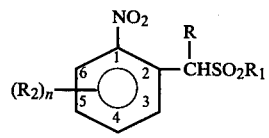

wherein
R is $C_{1-6}$ alkyl or alkanoyl, formyl or alkenyl or alkynyl having up to 4 carbon atoms;
$R_1$ is $C_{1-6}$ alkyl, phenyl or phenyl substituted with $C_{1-6}$ alkyl or alkoxy or halogen;
$R_2$ is independently hydrogen or the same as R or $R_1$, $NO_2$, CN, $CF_3$ or $C_{1-6}$ alkoxy or alkoxycarbonyl and
n is 0–4, which comprises the steps of
(a) reacting a compound having the formula

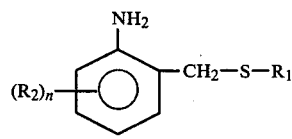

wherein $R_1$, $R_2$ and n are as defined above, with a peracid to form

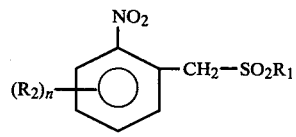

wherein $R_1$, $R_2$ and n are as defined above;
(b) reacting the product of step (a) with a compound of the formula

RZ          III in the presence of a base selected from the group consisting of alkali or alkaline earth oxides or hydroxides wherein R is as defined above except hydrogen; and Z is sulfate or tosylate radical or a halogen atom or RZ is a 1,4-Michael addition agent.

5. Process according to claim 4 wherein said reaction is conducted at temperatures within the range of from about −78° C. to 150° C.

6. Process according to claim 5 wherein R and $R_1$ are both $C_{1-6}$ alkyl radicals.

7. Process according to claim 6 wherein R and $R_1$ are both methyl radicals.

8. Process according to claim 7 wherein n is 1 and $R_2$ is 6-$CF_3$.

9. Process according to claim 7 wherein n is 2 and the $R_2$s are 4-Cl and 6-$CF_3$.

10. Process according to claim 6 wherein R is ethyl, $R_1$ is methyl, n is 1 and $R_2$ is 6-$CF_3$.

* * * * *